United States Patent [19]

Nivens et al.

[11] Patent Number: 5,487,981
[45] Date of Patent: Jan. 30, 1996

[54] APPARATUS FOR AND METHOD OF DETECTING/IDENTIFYING MICROBIAL CONTAMINATION IN ULTRA-PURE WATER SYSTEMS

[75] Inventors: David E. Nivens, Knoxville; James Q. Chambers, Concord; David C. White, Knoxville, all of Tenn.

[73] Assignee: The United States of America as represented by the Secretary of the Navy, Washington, D.C.

[21] Appl. No.: 99,384

[22] Filed: Jul. 30, 1993

[51] Int. Cl.$^6$ .............................. C12Q 1/24; C12M 1/34
[52] U.S. Cl. ............................ 435/30; 435/31; 435/34; 422/62; 422/81; 422/82; 422/82.02; 422/82.09; 436/52; 436/53; 436/63; 436/71; 204/403
[58] Field of Search .................... 435/30, 31, 34, 435/291; 422/62, 68.1, 81, 82, 82.01, 82.02, 82.09, 105, 110, 119; 436/50, 52, 53, 55, 63, 71; 204/153.1, 153.12, 400, 403; 250/356.1, 373; 73/61 R, 61.2

[56] References Cited

U.S. PATENT DOCUMENTS

| | | | |
|---|---|---|---|
| 4,912,332 | 3/1990 | Siebel et al. | 250/356.1 |
| 5,049,492 | 9/1991 | Sauer et al. | 435/30 |
| 5,246,560 | 9/1993 | Nekoksa et al. | 204/400 |

*Primary Examiner*—David A. Redding
*Attorney, Agent, or Firm*—Thomas E. McDonald; William F. McCarthy

[57] ABSTRACT

An apparatus for and a method of on-line detecting and assessing, in situ, the amount and characterization of microbial trace contamination in an associated ultra-pure water system is disclosed. The apparatus comprises, inter alia, a monitor/detector portion and an assessment/identification portion. The monitor/detector portion includes a contamination mass detector which nondestructively senses the presence of microbial biofilms in real time when grown upon the surface of a quartz crystal wafer portion of the contamination mass detector. The assessment/identification portion is configured to provide quantitative analysis of the microbial biofilms formations based on signature biomarker cellular components. A programmable controller is configured to integrate these and other portions into an automated apparatus, which is capable of providing real time chemical countermeasures to prevent the potential deleterious effect of the microbial trace contamination uncovered.

13 Claims, 7 Drawing Sheets

■ Standard    □ SFE Extraction

APPARATUS FOR AND METHOD OF DETECTING/IDENTIFYING MICROBIAL CONTAMINATION IN ULTRA-PURE WATER SYSTEMS

BACKGROUND OF THE INVENTION

1. Field of the Invention

The present invention relates generally to the detection of microbial contamination in ultra-pure water systems, but more specifically to the detection and/or identification of microbial biofilms which are predisposed to form on surfaces of the ultra-pure water system where the sparse nutrients therein tend to accumulate.

2. Description of the Prior Art

The recovery of bacteria in high-quality water used for drinking and in ultra-pure water systems used to process integrated circuits or other electronic devices is a major problem. In ultra-pure water systems, any type of contamination is a major problem. The contamination of integrated circuits with microorganisms is an especially serious problem as these organisms have the potential to proliferate and destroy the function of the circuits. The organisms that colonize the ultra-pure water systems are initially bound or attached to the surfaces of the containment systems as biofilms because the surfaces are the sources of what little nutrient are available in these environments. A source of the bound organisms is from breakthrough or regrowth from other organisms that were insufficiently treated at the purification center, and, accordingly, recovered from the disinfectant treatment or avoided the treatment. Another source of bound organisms is from true breakdown from contamination by back siphonage or cross connections in the ultra-pure water systems.

The contamination problem is further complicated by the strong tendency of organisms in these oligotrophic (nutrient-poor) environments to attach to particles or surfaces with the formation of biofilms. These biofilms are anchored to the surfaces by exopolymer polysaccharides (EPS) which make them extremely difficult to treat and to dislodge quantitatively for prior art culturable methods by which they are routinely detected.

The prior art evaluation methods that rely on the culturing of these organisms suffer several serious deficiencies. Organisms from these extreme environments, i.e., high-quality or ultra-pure water systems, are notoriously difficult to culture so that standard plate count techniques will not give an accurate estimate. The problem of viable but not culturable bacteria is a well known and accepted concept in public health microbiology. For example, the *cholera* causing organism *Vibrio cholera* when starved forms minicells that are often not culturable, but readily initiate the disease when the water is consumed. Not only do the microorganisms not grow out readily on attempted isolation, but the growth, particularly, of autotrophic organisms found in very low nutrient water take several days to weeks to grow to detectable colonies. This delay is clearly not acceptable in ultra-pure water systems where continual control is essential. Many of the prior art microscopic techniques are not very sensitive. It often requires at least $10^5$ organisms/ml for reliable detection of contamination. Concentration by centrifugation or filtration with vital staining and microscopic examination requires that the water system be sampled, thereby creating the potential for additional contamination. These methods are also time consuming, and require trained operators for detection and identification. Moreover, the type(s) of bacteria involved in the contamination are not usually readily determined with the microscopic examination. It is possible to identify specific microbes using fluorescent labeled probes. This requires, however, that the organisms commonly contaminating the system be well known so that antibodies or gene probes can be developed.

A well known prior art method of enumerating bacteria is to recover them from water by filtration or from containment surfaces by mechanical or physical (ultrasonic) means. The bacteria are then cultured in pour plates of various nutrient media. There are various prior art methods that allow for the recovery of damaged bacteria so that they will eventually grow and form visible colonies in an assay system. If any of these techniques are to be accurate, two main features must be established. First, the bacteria must be quantitatively recovered from the biofilm or the filter so they can be plated in the nutrient media used for the colony formation. Second, the nutrient conditions must be able to grow every organism from a single cell to a colony of over $10^{6-9}$ cells. It is known in the prior art from experiments in seawater that the number of bacteria that can be counted directly on a filter after staining versus the number that can be determined by plate counts is between $10^2$ to $10^4$ times less. This problem is more clearly demonstrated by experience in soils where the attachment problem complicates the culturability problem. Here, often considerably less than 0.1% of detectable organisms can be cultured.

The problem of culturability is even worse in the high-quality or ultra-pure water systems because the bacteria in the "regrowth" condition which have been injured sublethally by disinfection treatment account for most of the increased bacterial contamination. The problem of infectious bacteria that are "infectious but not culturable" has recently become known in the prior art. The disinfection-injured bacteria in the ultra-pure water systems particularly those attached to particles or containment surfaces are known to be very difficult to culture. Accordingly these ultra-pure water systems are vulnerable to distribution of contaminated water having organisms that will colonize the surfaces of the distribution system with the concomitant health and property problems.

The prior art, as indicated hereinabove, teach some advances in the detection/identification of microbial contamination in high-quality or ultra-pure water systems. Insofar as can be determined, however, no prior art apparatus or method incorporates all of the features and advantages of the present invention.

OBJECTS OF THE INVENTION

Accordingly, a principal object of the present invention is to configure an apparatus, and, hence, to create a method to detect/assess, in real time, possible microbial contamination in an associated ultra-pure water system so that corrective action can commence as rapidly as is feasible.

A corollary object of the above principal object is to configure the apparatus, and, thus, create the method to detect/assess the microbial contamination in of the associated ultra-pure water system such that the microbial contamination will grow microbial biofilms which replicate, i.e., copy, the microbial biofilms growing in the associated ultra-pure water system.

An important object of the above corollary object is to configure the apparatus to be nondestructive in function so as not to inhibit or damage the copied microbial biofilms growing therein, thereby providing an accurate replication of the microbial biofilms growing on containment surfaces of the associated ultra-pure water system where the available sparse nutrients accumulate.

Yet another important object of the present invention is to configure the apparatus to include means upon which the copies of microbial biofilms can grow and be detected in an improved manner.

Still yet another important object of the present invention is not only to detect and assess, i.e., determine presence and quantity, the microbial contamination, but, also, to provide a definitive identification thereof in an improved manner.

SUMMARY OF THE INVENTION

In accordance with the foregoing stated objects, other objects, features and advantages, the present invention has as a primary purpose to detect/identify microbial contamination in an associated ultra-pure water system by growing microbial biofilms which replicate the microbial biofilms growing in the associated ultra-pure water system.

The essence of the present invention is in the recognition that microbial contamination, i.e., bacteria, in nutrient-poor water systems such as the previously mentioned associated ultra-pure water system, tend to move to and multiply on surfaces where the nutrients accumulate. Thus, the apparatus, according to the present invention, provides, inter alia, a surface where these nutrients can accumulate, and, accordingly, where replicate biofilms can develop. The apparatus is nondestructive, in operation, i.e., the biofilm copies are not inhibited in their growth or damaged in any way. The apparatus, then, provides a true picture of the microbial contamination in the associated ultra-pure water system based on an analysis of the biofilm copies.

The purpose of the present invention is carried out by configuring the apparatus to include, inter alia, a contamination mass detector, and an open circuit potential detector, which both act, independently, as detector portions, a super fluid extractor coupled at its input to an extractor pump device and at its output to a FAME (fatty acid methyl esters) device which coact to form an assessment/identification portion. All of the foregoing devices/portions are synergistically controlled by a programmable controller. More specifically, a replicated microbial biofilm is detected by monitoring a decrease in the resonance frequency of a quartz crystal wafer portion of the contamination mass detector, and/or a decrease in the open circuit potential of a gold top electrode pad attached to the quartz crystal wafer portion. For more robust applications, the open circuit potential can be measured by the open circuit potential detector. When either of the foregoing detectors detects microbial contamination, ultra-pure water (liquid phase) in the supercritical fluid extractor will be forced out with carbon dioxide ($CO_2$), and the supercritical fluid extractor pressurized and heated to form supercritical fluid-$CO_2$ (SCF-$CO_2$). The SCF-$CO_2$ is used as an extractant formed by the extractor pump device to remove neutral lipids from the supercritical fluid extractor. Subsequently, in situ derivatizing chemistry is performed on polar lipids in the supercritical fluid extractor and the resulting FAME are extracted with SCF-$CO_2$. The FAME are used as signature biomarkers of the replicated biofilm and/or liquid phase microorganisms. The polar lipid ester-linked fatty acids (PLFA), which are essentially phospholipids in microorganisms found in ultra-pure water systems, are analyzed on-line or off-line by capillary gas chromatography/mass spectrometry (GC/MS) by the FAME device.

BRIEF DESCRIPTION OF THE DRAWINGS

The previously stated objects, other objects, features and advantages of the apparatus and method according to the present invention will become more apparent from the following more particular description of the preferred embodiments taken in connection with the accompanying drawings, in which.

DESCRIPTION OF THE PREFERRED EMBODIMENTS

Figure 1:
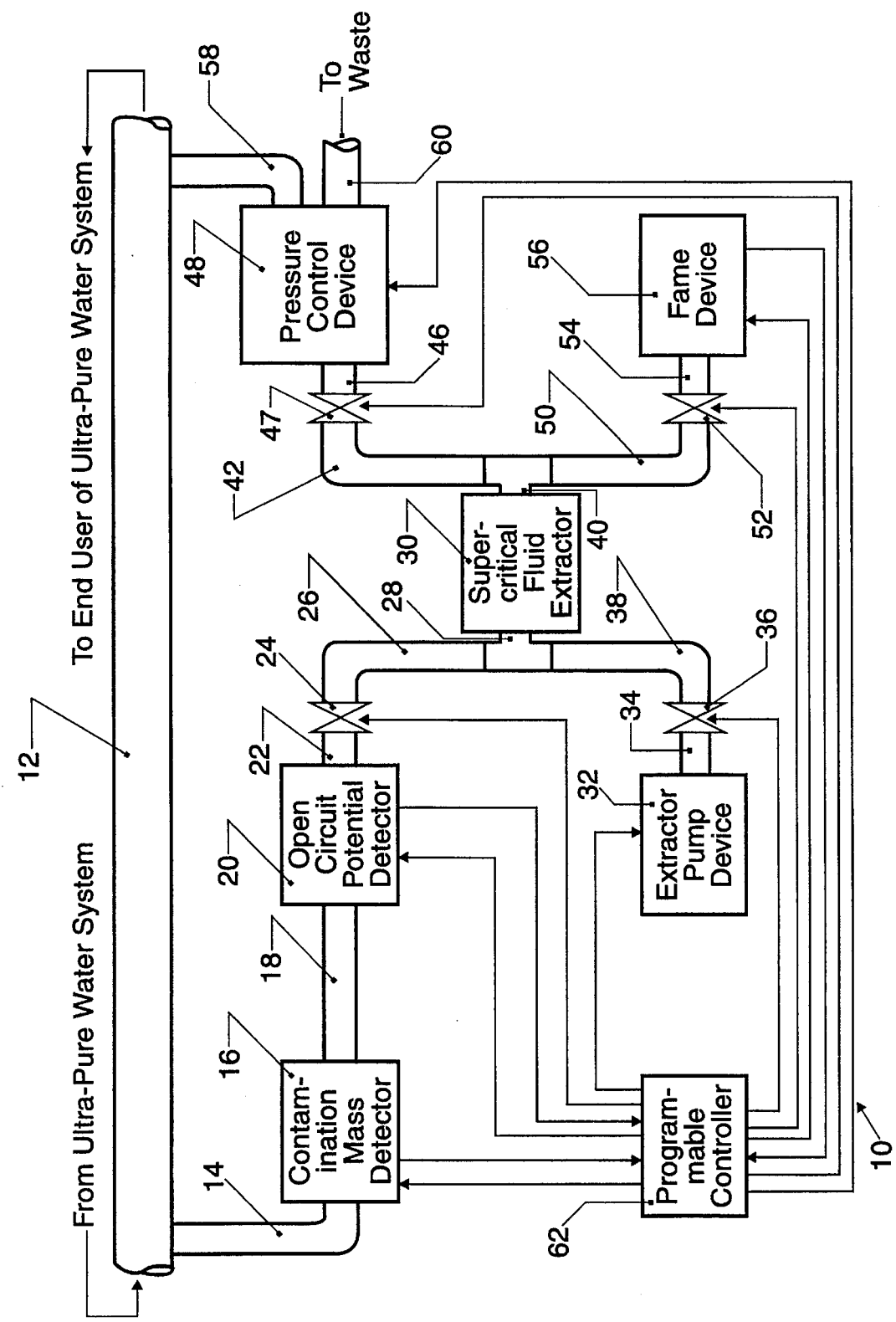
FIG. 1 is a schematic block diagram representation of a microbial contamination detection/identification apparatus suitable for carrying out the method according to the present invention including a contamination mass detector portion, an open circuit potential detector, and a supercritical fluid extractor.

The present invention represents the automated coaction of several elements into an apparatus capable of detecting microbial contamination in ultra-pure water systems in real time so that control countermeasures can be applied quickly to minimize damage to health and/or property. Referring then to FIG. 1, a microbial contamination detector/identification apparatus 10 suitable for carrying out the foregoing is operatively connected to a mainstream pipeline 12 of an associated ultra-pure water system (not shown). The apparatus 10 monitors ultra-pure water from the associated ultra-pure water system via an input sidestream pipeline 14, which is operatively connected between the aforementioned mainstream pipeline 12 and a contamination mass detector 16. The contamination mass detector 16 is mass-sensitive and is configured to respond to all interfacial mass changes, and, accordingly, provides measurements of the colonization of bound/attached microbes. In one embodiment of the present invention, the water flows from the contamination mass detector 16 via a pipeline 18 into an open circuit potential detector 20, which is an electrochemical cell for measuring the open circuit potential. The open circuit potential detector 20 furnishes open circuit potential information, which can also be furnished by the contamination mass detector 16 (to be discussed hereafter in conjunction with FIG. 2). The open circuit potential detector 20, however, gives better results in more robust environments of temperature and pressure. For purposes of the present invention, the open circuit potential detector 20 includes a working electrode (not shown) and a reference electrode (not shown) where the potential difference, i.e., the open circuit potential, is measured over time in response to the growth of different bacteria and combinations of bacteria on the surfaces thereof.

To continue, and still referring to FIG. 1, a fluid output of the open circuit potential detector 20 is operatively connected via a pipeline 22 to a fluid input of a first control value 24. A fluid output of the first control value 24 via a pipeline 26 and a T-pipeline connector 28 is operatively connected to a fluid input of a supercritical fluid extractor 30. Likewise, a fluid output of an extractor pump device 32 is operatively connected via a pipeline 34 to a fluid input of a second control valve 36. A fluid output of the second control valve 36 is operatively connected via a pipeline 38 and the aforementioned T-pipeline connector 28 to the fluid input of the supercritical fluid extractor 30.

As also shown in FIG. 1, a fluid output of the supercritical fluid extractor 30 is operatively connected via a T-pipeline connector 40 and a pipeline 42 to a fluid input of a third control valve 44. A fluid output of the third control valve 44 via a pipeline 46 is operatively connected to a fluid input of a pressure control device 48. Likewise, the same fluid output of the supercritical fluid extractor 30 is operatively connected via the T-pipeline connector 40 and a pipeline 50 to a fluid input of a fourth control valve 52. A fluid output of the fourth control valve 52 via a pipeline 54 is operatively connected to a fluid input of a FAME device 56. The FAME device 56 is configured to perform on-line or off-line chemistry by capillary gas chromatograph/mass spectrometry (GC/MS).

Continuing, one fluid output of the pressure control device 48 via an output sidestream pipeline 58 is operatively connected back to the mainstream pipeline 12 of the associated ultra-pure water system. Another fluid output of the pressure control device 48 via a pipeline 60 is operatively connected to a waste receptacle (not shown). Finally, as shown in FIG. 1, a programmable controller 62 is operatively connected to electrical inputs and/or outputs of the aforementioned elements so as to control all aspects of their operation. The programmable controller 62 is programmed to regulate various responses to microbial contamination. A more detailed discussion of the operation of the present invention will be presented in the "STATEMENT OF THE OPERATION" Section of the present application hereintofollow.

Figure 2:
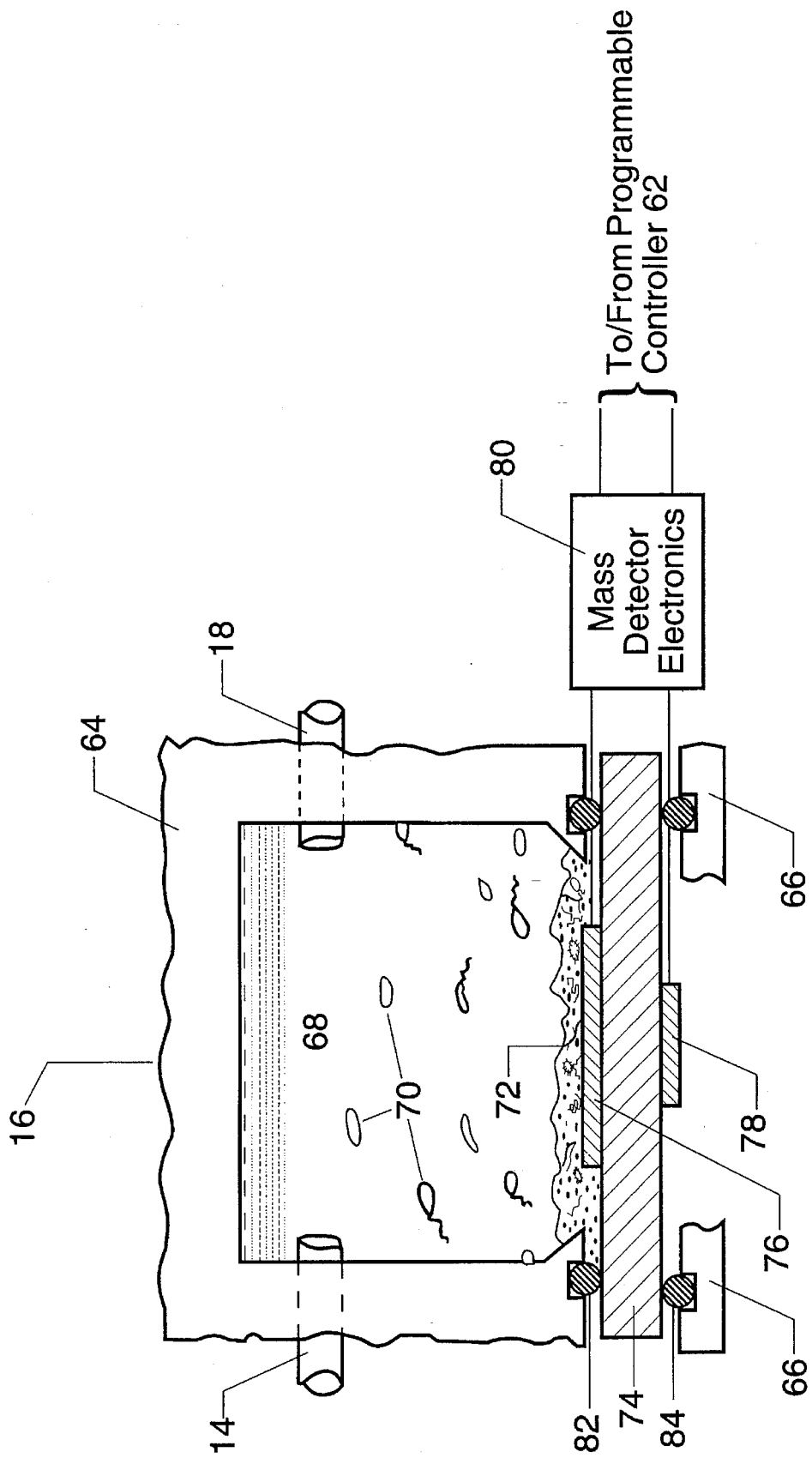
FIG. 2 is a schematic pictorial diagram of the contamination mass detector of FIG. 1 depicting the essential components thereof including a quartz crystal wafer portion.

Referring now to FIGS. 1 and 2 as viewed concurrently, but specifically to FIG. 2, the contamination mass detector 16 comprises a top water containment portion 64 and a bottom support portion 66 which forms the container for ultra-pure water 68. Liquid phase microbial contamination 70 (including particles) in the ultra-pure water 68, over time, grows a microbial biofilm 72 upon a quartz crystal wafer 74. The quartz crystal wafer 74 is sandwiched between a top electrode pad 76 and a bottom electrode pad 78, both being bonded to the top and bottom surfaces, respectively, of the quartz crystal wafer 74. It should be noted that, as shown in FIG. 2, the microbial biofilm 72 (including particles) also grows upon the top electrode pad 76. As shown, a mass detector electronics 80 is operatively connected between the top and bottom electrode pads 76 and 78, and the programmable controller 62. As connected and in response to inputs from the programmable controller 62, the mass detector electronics 80 via the top electrode pad 76 and the bottom electrode pad 78 induces an oscillating electric field in the quartz crystal wafer 74 upon which they are bonded. This oscillating electric field produces a mechanical oscillation in the quartz crystal wafer 74. This mechanical oscillation (displacement) is parallel to the quartz crystal wafer 74 (top and bottom surfaces). The mass detector electronics 80 is also configured to read the open circuit potential between the top of the electrode pad 76 and a reference electrode (not shown). This information is fed back to the programmable controller 62. In addition, the mass detector electronics 80 is configured to couple controlled-potentials and/or controlled currents to the top and bottom electrode pads 76 and 78 in response to inputs from the programmable controller 62. To complete the configuration of the contamination mass detector 16, the quartz crystal wafer 74 is sealed between a top O-ring 82 and a bottom O-ring 84. As shown, only the top surface of the quartz crystal wafer 74 and the top electrode pad 76 are in contact with the ultra-pure water 68.

The contamination mass detector 16 of the present invention is a modification of the well known quartz crystal microbalance (QCM). The QCM, however, has only been used in liquid applications for about ten (10) years because of the belief that excessive viscous loading would prohibit its use. This is not the case in actual operation. On the contrary, at constant pressure and temperature it is only required to provide laminar flow conditions via the input sidestream pipeline 14 into the contamination mass detector 16 through the pipeline 18 in order to obtain stable frequency information from the quartz crystal wafer 74. This laminar flow is controlled, inter alia, by the pressure control device 48 of FIG. 1 and a pump (not shown) positioned between the input sidestream pipeline 14 and the contamination mass detector 16. Laminar flow conditions are maintained at flow rates within the range of 0 to 15 ml/minute.

Figure 3:
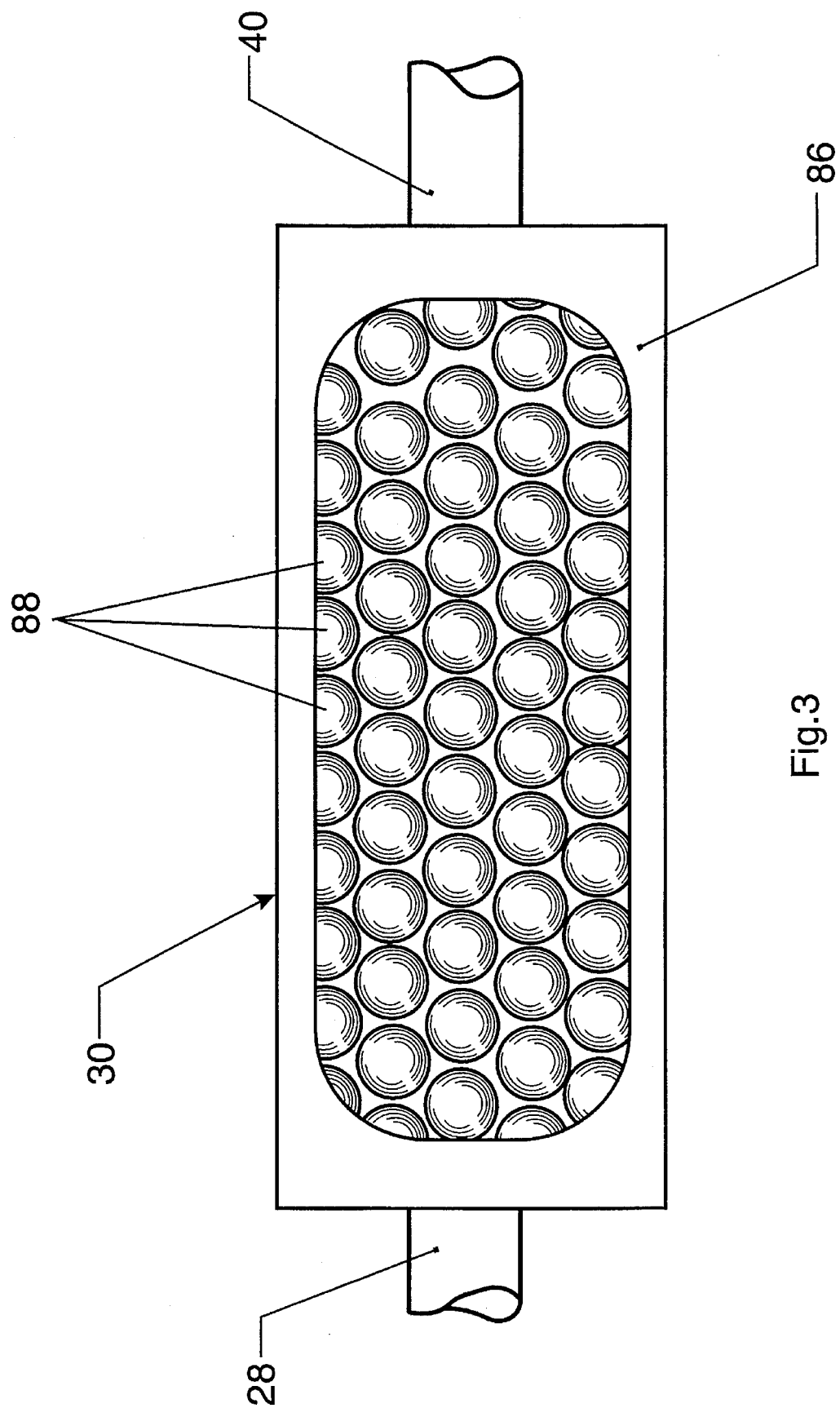
FIG. 3 is a schematic pictorial diagram of the supercritical fluid extractor of FIG. 1 depicting the essential components thereof.

Referring now to FIGS. 1 and 3 as viewed concurrently, but specifically to FIG. 3, a cutaway pictorial diagram of the supercritical fluid extractor 30 of FIG. 1 is shown. The supercritical fluid extractor 30 is configured to collect, over time, microbial contamination, and, also, replicate microbial biofilms from the ultra-pure water flowing therethrough. The supercritical fluid extractor 30 comprises a cylindrical housing 86 of a predetermined volume which is packed with a plurality of spherical beads 88. The plurality of spherical beads 88 increase the surface area and decrease the dead volume of the supercritical fluid extractor 30. For purposes of the present invention, the cylindrical housing 86 is fabricated of stainless steel and has a volume of about 10 ml. The plurality of spherical beads 88 are also fabricated of stainless steel and have diameters of about 1 mm each. If desired, porous stainless steel frits (not shown) can be used at the end of the cylindrical housing 86 to contain the plurality of spherical beads 88 and trap the liquid phase microbial contamination 70. It should be mentioned that the volume of the cylindrical housing 86 and the diameter of the plurality of spherical beads 88 will vary depending on operational conditions such as time and pressure.

STATEMENT OF THE OPERATION

Referring now to FIGS. 1, 2 and 3 as viewed concurrently, the associated ultra-pure water system (not shown) is monitored through the input sidestream pipeline 14 by the contamination mass detector 16 which measures the initial colonization of the microbial biofilm 72. The contamination mass detector 16 is also configured to measure the open circuit potential. If desired, in another embodiment configured for more robust applications, the flow of water is into the open circuit potential detector 20 where the open circuit potential is measured between a working electrode (not shown) and a reference electrode (not shown). The water next passes through the first control valve 24 into the supercritical fluid extractor 30 and through the third control value 44 into the pressure control device 48. In normal operation, the pressure control device 48 controls the pressure in the flowing water and returns it via the output sidestream pipeline 58 to the mainstream pipeline 12 to an end user of the associated ultra-pure water system. In the alternative, the water is discharged to waste via the pipeline 60 of the pressure control device 48. Once the contamination mass detector 16 and/or the open circuit potential detector 20 sense(s) significant contamination with biofilm formation, by action of the programmable controller 62 the first control valve 24 is caused to close, the second control valve 36 is caused to open while the third and fourth control valves 44 and 52 remain opened and closed, respectively. With this action, the extractor pump device 32 purges the water from the supercritical fluid extractor 30 with low pressure $CO_2$. Once the supercritical fluid extractor 30 is free of water, the third control valve 44 is closed and the supercritical fluid extractor 30 is heated (by a heating coil, not shown) to 50° C. and pressurized with $CO_2$ to a maximum pressure of 400 atmospheres atm. This action produces supercritical fluid $CO_2$ in the supercritical fluid extractor 30. At equilibrium, the fourth control valve 52 is opened to quantitatively remove neutral lipids from the supercritical fluid extractor 30. The extractor pump device 32 maintains the pressure at 400 atm during the entire removal process. The pressure in the supercritical fluid extractor 30 is released by closing the second control valve 36 after the neutral lipids are quantitatively removed. During the supercritical fluid extraction operation, potentials are applied to the top and bottom electrode pads 76 and 78 of the contamination mass detector 16 and the working electrode (not shown) and the reference electrode (not shown) of the open circuit potential detector 20 to remove the microbial biofilms to regenerate the aforementioned electrodes for recolonization. If desired, the neutral lipids can be processed off-line or on-line by capillary gas chromatography/mass spectrometry (GC/MS). In one embodiment of polar lipid analysis, a small volume (about 0.05 times the volume of the supercritical fluid extractor 30) of trimethylphenolammonium hydroxide (TMPA) in methanol is added to the supercritical fluid extractor 30 via a control valve (not shown). The supercritical fluid extractor 30 is then heated to 80° C. and subsequently pressurized to 400 atm by opening the second control valve 36. The pressure is again maintained at 400 atm by the extractor pump device 32 while the polar lipid FAME are being quantitatively removed from the supercritical fluid extractor 30. The FAME can be collected and analyzed on-line or off-line by the FAME device 56. In the on-line configuration, the FAME are collected in a direct interface portion (not shown) of the FAME device 56 and analyzed by GC/MS. In the off-line configuration of the FAME device 56, the FAME are adsorbed to a solid phase or collected in an autosample vial (not shown) containing solvent and subsequently analyzed by GC/MS. The FAME are biomarkers for microorganisms that are commonly found in ultra-pure water systems. Resultant FAME profiles are compared in the programmable controller 62 against library FAME profiles to assess the microbial contamination (see FIG. 7b). After complete removal of the polar lipid derived FAME, the second control valve 36 is closed, and the supercritical extractor 30 is depressurized. To initialize the microbial contamination detector/identification apparatus 10 for a new analysis, the fourth control valve 52 is closed and the first and third control valves 24 and 44 are opened. The programmable controller 62 is used to control all aspects of the operation, according to the present invention, and is programmed to regulate various responses to the microbial biofilm 72 in the contamination mass detector 16.

Figure 4:
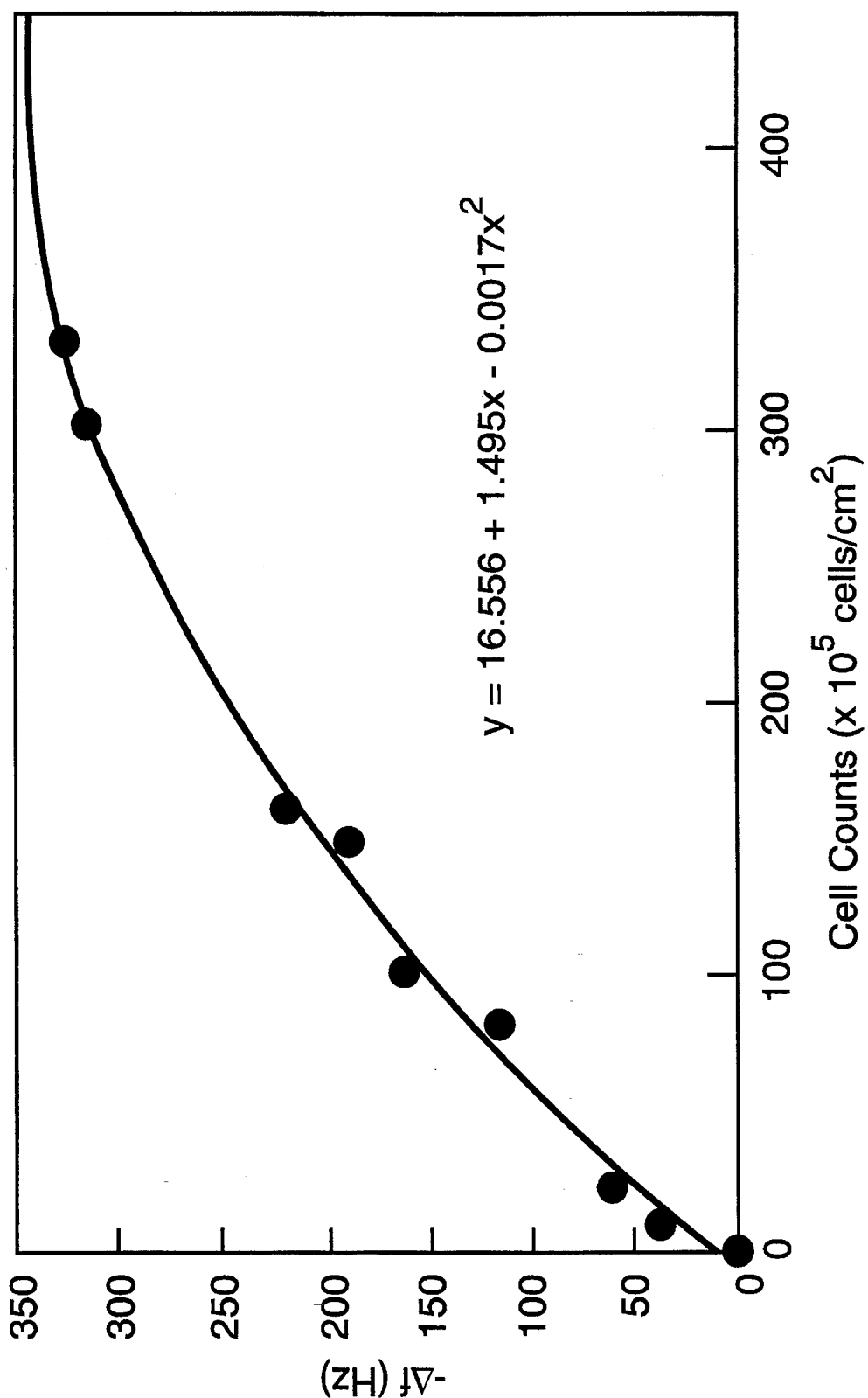
FIG. 4 is a graph which shows the frequency shift in Hertz (Hz) versus the direct count of bacteria (microbial biofilm) growth on the quartz crystal wafer portion of the contamination mass detector of FIGS. 1 and 2.
Figure 5:
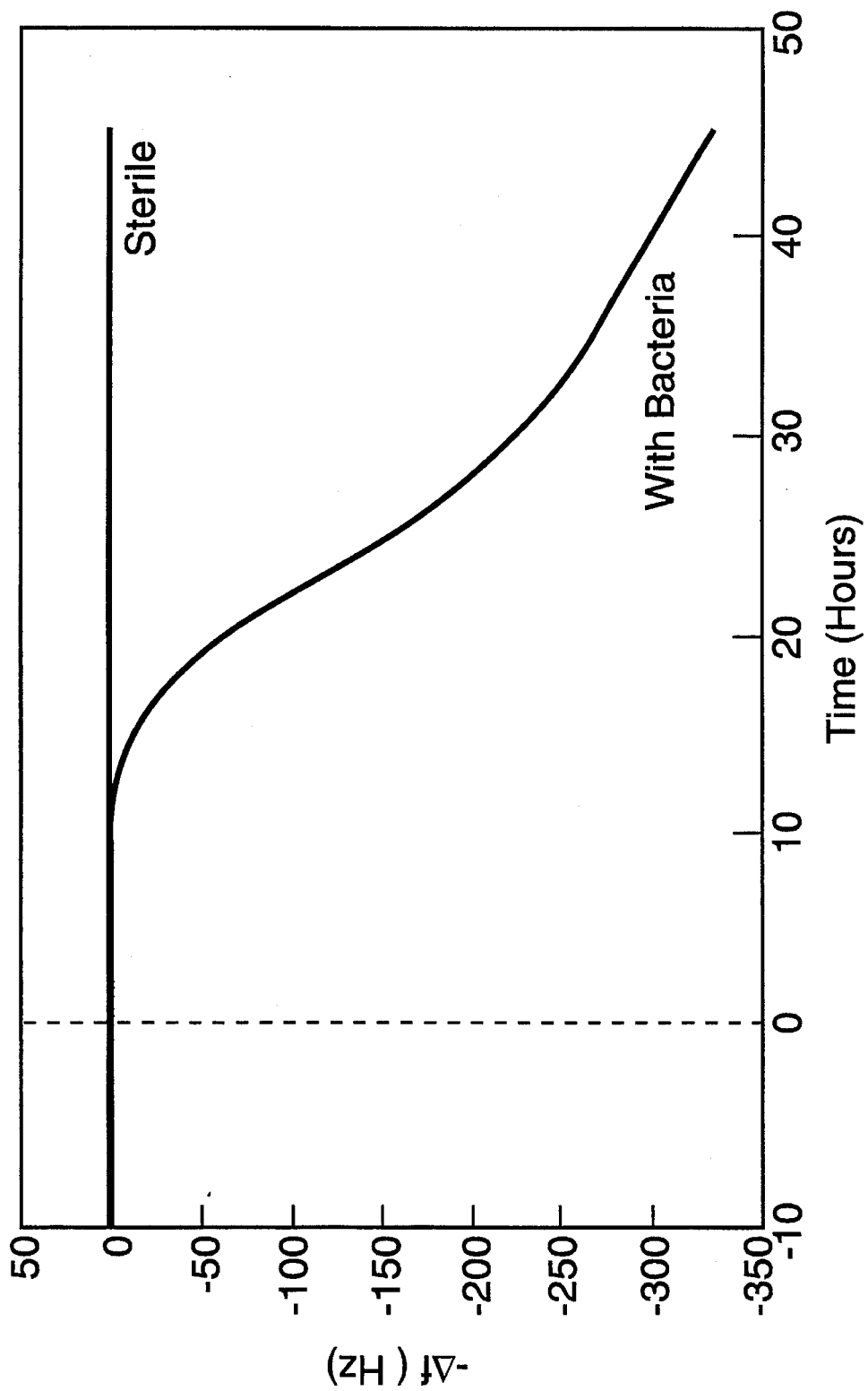
FIG. 5 is a graph which shows the frequency shift in Hz versus the time in hours for a controlled/sterile condition of growth, i.e., no inoculation, on the quartz crystal wafer portion of the contamination mass detector of FIGS. 1 and 2, compared with inoculated growth of bacteria thereon.

To continue, for purposes of the present invention, the quartz crystal wafer 74 of FIG. 2 is a 5 MHz AT-cut quartz crystal of 25 mm in diameter. The top and bottom electrode pads 76 and 78 are deposited upon the quartz crystal wafer 74 and are comprised of gold. Above the detection limit for the microbial biofilm 72, the difference in unit density between it and the ultra-pure water 68 will cause the resonant frequency of the quartz crystal wafer 74 to decrease. In a standard operating mode, a broadband oscillator portion (not shown) of the mass detector electronics 80 causes the quartz crystal wafer 74 to vibrate and the frequency of the vibration is monitored by a frequency counter (not shown) portion of the mass detector electronics 80. As an example, when the contamination mass detector 16 is exposed to the ultra-pure water 68 (sterile water), the frequency remains stable (see FIG. 5). During a microbial contamination event, the formation of the microbial biofilm 72 causes the frequency to decrease (see FIG. 5). At microbial biofilm 72 densities greater than $10^5$ *Pseudomonas cepacia* cells/cm$^2$ the relationship between the attached bacteria and a decrease in frequency is monotonic as shown in FIG. 4. If fluctuations in the hydraulic pressure or temperature of the ultra-pure water 68 in contact with the quartz crystal wafer 74 becomes significant, pressure and/or temperature compensation will be applied. A pressurizing device (not shown) will apply incremental changes in pressure to the bottom surface of the quartz crystal wafer 74. When the applied pressure is equal and opposite to the hydraulic pressure on the top surface of the quartz crystal wafer 74, the frequency of unstressed quartz crystal wafer 74 can be determined by the programmable controller 62. For temperature compensation, the programmable controller 62 measures the temperature of the unstressed quartz crystal wafer 74 with a resistance temperature detector (not shown) and determines the offset frequency and compensates therefor.

Figure 6A:
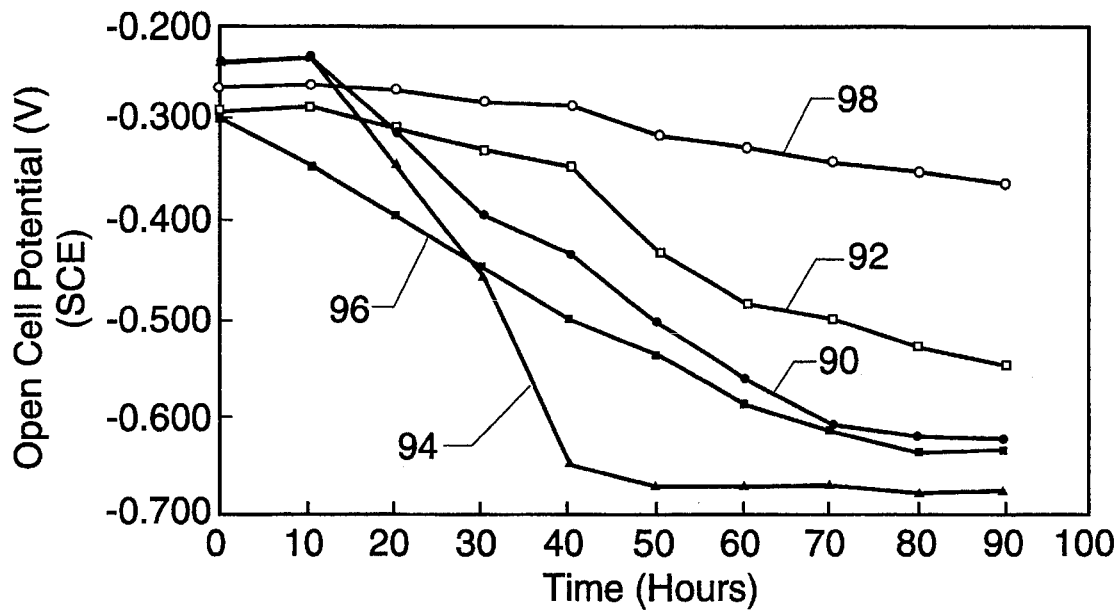
FIGS. 6a and 6b show graphs of the average change in the open circuit potential over time at time carbon steel electrodes (not shown) of the open circuit potential detector of FIG. 1 in response to the growth of different bacteria and combinations of bacteria on the surface of the carbon steel electrodes.
Figure 6B:
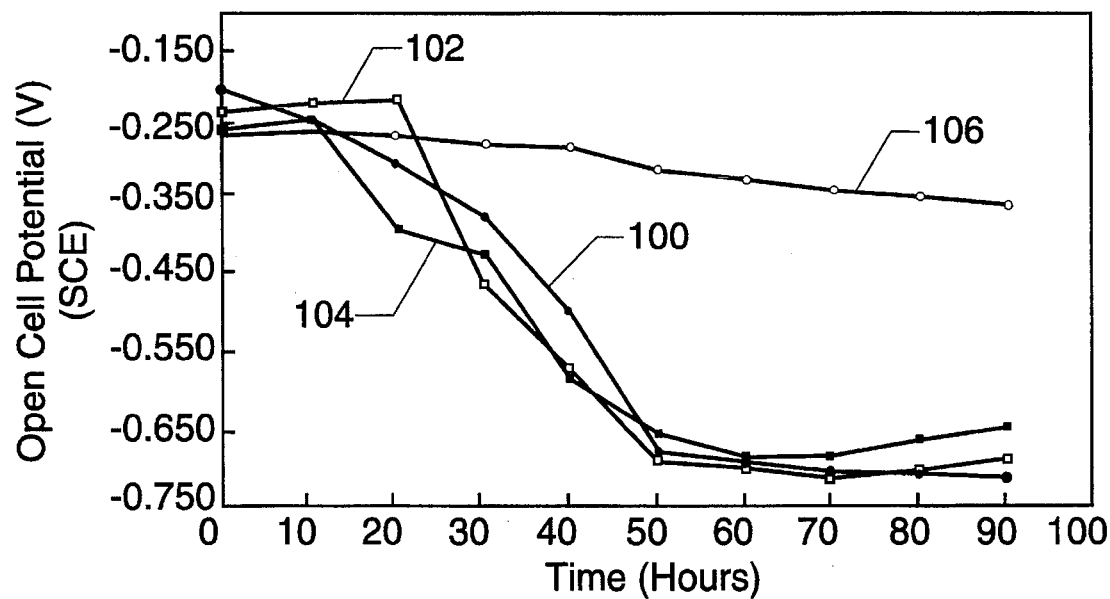

The open circuit potential is determined by measuring the potential difference between the gold top electrode pad 76 and a reference electrode (not shown) in the contamination mass detector 16 or with the open circuit potential detector 20, via working and reference electrodes (not shown). For purposes of the present invention, a suitable reference electrode could be a silver/silver chloride or calomel electrode fashioned into a Luggin probe. The data in FIGS. 6a and 6b show decreases in the open circuit potential with colonization of a carbon steel working electrode by different bacteria and combinations of bacteria. In FIG. 6a, curves 90, 92, 94, and 96, corresponding respectively to bacteria growths on the electrode of (1) *H. alvei*, (2) *D. gigas*, (3) *H. alvei* plus *D. gigas*, and (4) Bacillus plus *H. alvei* plus *D. gigas*, is compared with curve 98 for a sterile electrode control. In FIG. 6b, curves 100, 102, and 104, corresponding respectively to bacteria growths on the electrode of (1) Bacillus, (2) Bacillus plus *H. alvei*, and (3) Bacillus plus *D. gigas*, is compared with curve 106 for a sterile electrode control.

Figure 7A:
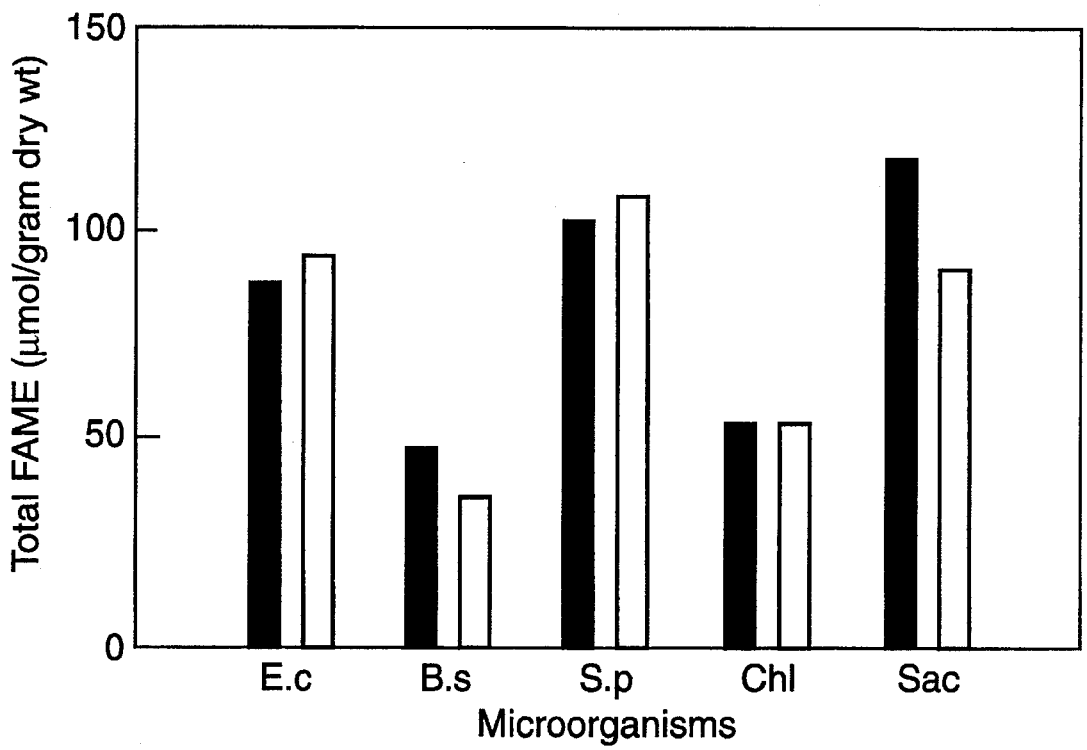
FIGS. 7a and 7b show graphs depicting the validity of the recovery of total fatty acids from bacteria, algae and yeast by supercritical fluid extraction in conjunction with the supercritical fluid extractor of FIGS. 1 and 3.
Figure 7B:
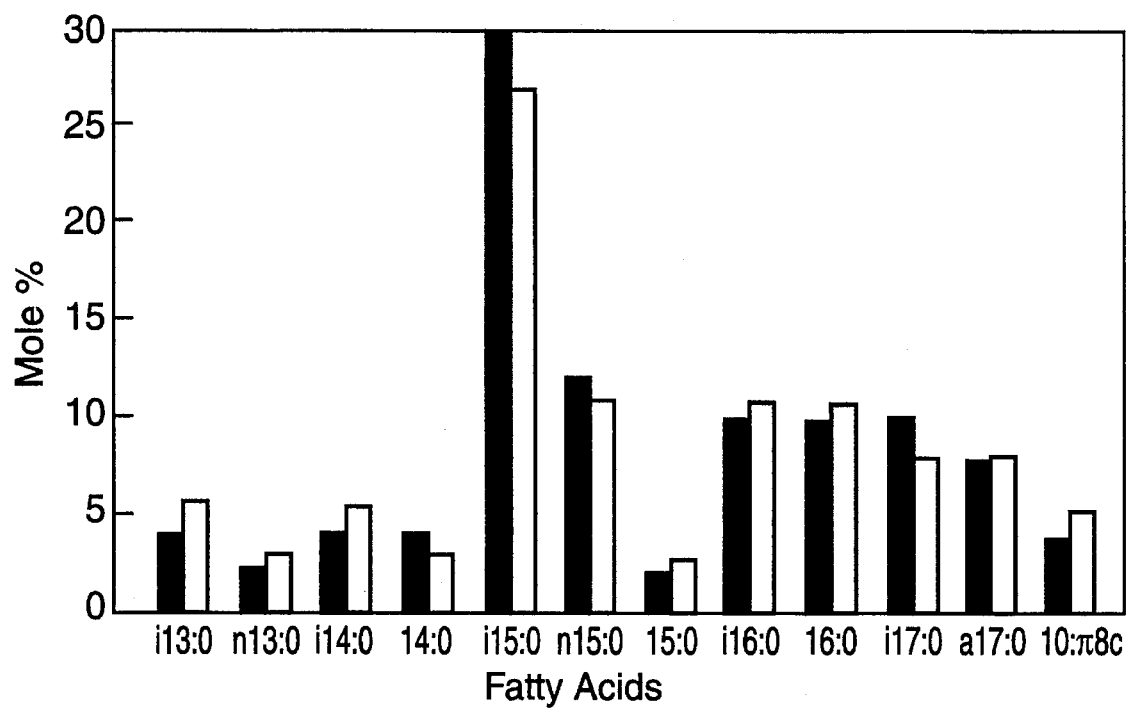

The method according to the present invention involves the supercritical fluid extraction of neutral lipids, followed by derivatization/supercritical fluid extraction of polar lipids which are quantitative measures of the viable or potentially viable microbes present in biofilms. The extraction of the polar lipids requires either of two procedures. The first procedure involves in situ derivatization of ester-linked fatty acids with a methylating reagent to form the fatty acid methyl esters (FAME) by transesterification. The quantitative transmethylation of the ester linked fatty acids of a number of algae, fungi, and bacteria using the agent TMPA is shown in FIG. 7a. These algae, fungi, and bacteria include *Escherichia coli, Bacillus subtilis, Spiruline platensis, Chlorella sp.*, and *Saccharomyces cervisine*, respectively labelled E.c., B.s., S.p., Chl., and Sac. in FIG. 7a. The fact that the procedure is not selective of any portion of the total pattern of ester-linked fatty acids is established by the data of FIG. 7b, which shows mole percentages of individual fatty acids recovered from *Bacillus subtilis*. The supercritical fluid extraction method is established by comparison with a standard method of lipid extraction using chloroform/methanol/water, which has been established as quantitative over many years. The second procedure involves the direct extraction of the polar lipids from the microbial biofilm. These phospholipids can be readily identified using the prior art method of fast atom bombardment. In FIGS. 7a and 7b, the mole values obtained by the supercritical fluid extraction method are indicated by light vertical bars and the values obtained by the standard liquid method of lipid extraction are indicated by dark vertical bars.

The present invention can be used in other than systems containing ultra-pure water. It can be used in the analysis of municipal or any water system where an on-line nondestructive method including supercritical fluid extraction would be beneficial.

To these skilled in the art, many modifications and variations of the present invention are possible in light of the above teachings. It is therefore to be understood that the present invention can be practiced otherwise than as specifically described herein and still be within the spirit and scope of the appended claims.

What is claimed is:

1. A method of on-line detection of the presence of microbial contamination and quantitatively assessing the microbes in an associated ultra-pure water system comprising the steps of:

monitoring ultra-pure water flowing from said associated ultra-pure water system to detect the presence of microbial contamination;

detecting over time the growth of microbial biofilms which replicate said microbial contamination in said associated ultra-pure water system; and assessing, in real time, quantitative measures of microbes present in said microbial biofilms indicated by the monitoring step and the detecting step.

2. The method of claim 1 wherein the detecting step comprises the steps of:

measuring, in a first step, the initial colonization of a microbial biofilm formed from said microbial contamination; and measuring, in a second step, over time, the open circuit potential of said ultra-pure water flowing from said associated ultra-pure water system to detect the growth of said microbial biofilms which replicate said microbial contamination.

3. The method of claim 1 wherein the monitoring step further comprises the step of:

controlling the pressure and the flow rate of said ultra-pure water flowing from said associated ultra-pure water system within respective ranges so as to create a laminar flow condition.

4. The method of claim 1 wherein the assessing step further comprises the step of:

collecting, over time, microbial contamination of said ultra-pure water in a supercritical fluid extractor to form another microbial biofilm which replicates said microbial contamination.

5. The method of claim 4 wherein the assessing step further comprises the steps of:

extracting, in a first step, quantitatively from said supercritical fluid extractor neutral lipids of said another microbial biofilm; and extracting, in a second step, quantitatively from said supercritical fluid extractor polar lipids of said another microbial biofilm, said neutral lipids and said polar lipids being quantitative measures of microbes in said another microbial biofilm.

6. The method of claim 5 wherein the second extracting step includes derivatizing said polar lipids.

7. The method of claim 5 wherein the first extracting step comprises the steps of:

pumping supercritical carbon dioxide extractant into said supercritical fluid extractor; and purging said supercritical fluid extractor to quantitatively extract said neutral lipids.

8. The method of claim 2 further comprising the step of:

applying potentials to top and bottom electrode pads associated with the first measuring step and the second measuring step to remove said microbial biofilms which replicate said microbial contamination so that recolonization can take place.

9. The method of claim 7 wherein said neutral lipids are processed off-line by capillary gas chromatography/mass spectrometry (GC/MS).

10. The method of claim 6 wherein said polar lipids are derivatized from said another microbial biofilm to form fatty acid methyl esters (FAME) which are extracted by use of supercritical carbon dioxide.

11. The method of claim 3 wherein the flow rate is controlled within the range of 0 to 15 ml/minute.

12. A method of on-line detection of the presence of microbial contamination and quantitatively assessing the microbes in an associated ultra-pure water system comprising the steps of:

monitoring ultra-pure water flowing from said associated ultra-pure water system to detect the presence of microbial contamination;

detecting over time the growth of microbial biofilms which replicate said microbial contamination in said associated ultra-pure water system; and assessing, in real time, quantitative measures of microbes present in said microbial biofilms indicated by the monitoring step and the detecting step, including collecting, over time, microbial contamination of said ultra-pure water in a supercritical fluid extractor to form another microbial biofilm which replicates said microbial comtamination.

13. A method of on-line detection of the presence of microbial contamination and quantitatively assessing the microbes in an associated ultra-pure water system comprising the steps of:

monitoring ultra-pure water flowing from said associated ultra-pure water system to detect the presence of microbial contamination, the monitoring step including controlling the presssure and the flow rate of said ultra-pure water flowing from said associated ultra=pure water system within respective ranges so as to create a laminar flow condition;

detecting over time the growth of microbial biofilms which replicate said microbial contamination in said associated ultra-pure water system, the detecting step including first measuring the initial colonization of a microbial biofilm formed from said microbial cpntamination and then measuring over time the open circuit potential of said ultra-pure water flowing from said associated ultra-pure water system to detect the growth of said microbial biofilms which replicate said microbial contamination; and assessing, in real time, quantitative measures of microbes present in said microbial biofilms indicated by the monitoring step and the detecting step.

* * * * *